(12) United States Patent
Kromer et al.

(10) Patent No.: US 7,629,361 B2
(45) Date of Patent: Dec. 8, 2009

(54) SALT OF (S)-PANTOPRAZOLE AND ITS HYDRATES

(75) Inventors: Wolfgang Kromer, Constance (DE); Bernd Müller, Constance (DE); Stefan Postius, Constance (DE); Wolfgang-Alexander Simon, Constance (DE); Ernst Sturm, Constance (DE); Guido Hanauer, Constance (DE)

(73) Assignee: NYCOMED GmbH, Constance (DE)

( * ) Notice: Subject to any disclaimer, the term of this patent is extended or adjusted under 35 U.S.C. 154(b) by 890 days.

(21) Appl. No.: 10/489,659

(22) PCT Filed: Jul. 26, 2003

(86) PCT No.: PCT/EP03/08269

§ 371 (c)(1),
(2), (4) Date: Mar. 15, 2004

(87) PCT Pub. No.: WO2004/013126

PCT Pub. Date: Feb. 12, 2004

(65) Prior Publication Data

US 2004/0248940 A1    Dec. 9, 2004

(30) Foreign Application Priority Data

| Jul. 29, 2002 | (DE) | 102 34 617 |
| Dec. 6, 2002 | (EP) | 02027275 |
| May 30, 2003 | (EP) | 03012411 |

(51) Int. Cl.
*A61K 31/4439* (2006.01)
*C07D 401/12* (2006.01)

(52) U.S. Cl. .................... 514/338; 546/273.7
(58) Field of Classification Search ........... 546/273.7; 514/338
See application file for complete search history.

(56) References Cited

U.S. PATENT DOCUMENTS

| 4,738,974 A | 4/1988 | Brändström |
| 4,758,579 A | 7/1988 | Kohl et al. |
| 5,635,520 A | 6/1997 | Uda |
| 5,714,504 A | 2/1998 | Lindberg et al. |
| 5,888,535 A | 3/1999 | Gray |
| 6,002,011 A | 12/1999 | Kato et al. |
| 6,124,464 A * | 9/2000 | Hogberg et al. ......... 546/273.7 |
| 6,365,184 B1 | 4/2002 | Depui et al. |
| 6,410,569 B1 * | 6/2002 | Kohl ......................... 514/338 |
| 6,875,872 B1 * | 4/2005 | Lindberg et al. ......... 546/273.7 |

FOREIGN PATENT DOCUMENTS

| EP | 0005129 | 10/1979 |
| EP | 166287 | 1/1986 |
| EP | 0174726 | 3/1986 |
| EP | 0268956 | 6/1988 |
| WO | WO 92/08716 | 5/1992 |
| WO | WO 94/24867 | 11/1994 |
| WO | WO 94/25028 | 11/1994 |
| WO | WO 94/27988 | 12/1994 |
| WO | WO 96/01624 | 1/1996 |
| WO | WO 96/24338 | 8/1996 |
| WO | WO 97/41114 | 11/1997 |
| WO | WO 98/54171 | 12/1998 |
| WO | WO 99/32091 | 7/1999 |
| WO | WO 00/10995 | 3/2000 |

OTHER PUBLICATIONS

Brittain et al., "Polymorphism in Pharmaceutical Solids", NY: Marcel Dekker, Inc., 1999, pp. 126-181, 183-226.*
Vippagunta et al., "Crystalline Solids", Advanced Drug Delievery Reviews 48 (20010 3-26.*
US Pharmacopia #23, National Formulary #18 (1995), 1843-1844.*
Doelker, "PhysiochemicaL behavior, etc.," S.T.P. Pharma Pratiques (1999), 9(5), 399-409 and english translation, pp. 1-33.*
CMU Pharmaceutical polymorphism, internet, p. 1-3 (2002) (printout Apr. 3, 2008).*
Singhal et al., "Drug Polymorphism . . . " Advanced drug delivery reviews 56, p. 335-347 (2004).*
RN 259669-63-1 Mar. 21, 2000.*

* cited by examiner

*Primary Examiner*—Patricia L Morris
(74) *Attorney, Agent, or Firm*—The Nath Law Group; Joshua B. Goldberg; Sheldon M. McGee

(57) ABSTRACT

The invention relates to (−)-pantoprazole magnesium and its hydrates and to medicaments comprising these compounds.

20 Claims, 3 Drawing Sheets

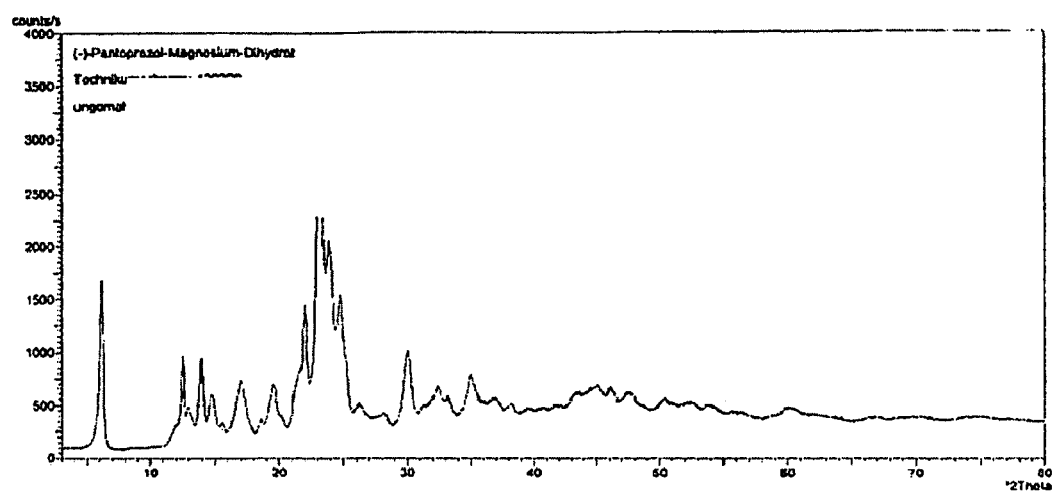
Figure 1: X-ray powder diffraction diagram of (-)-pantoprazole magnesium dihydrate.

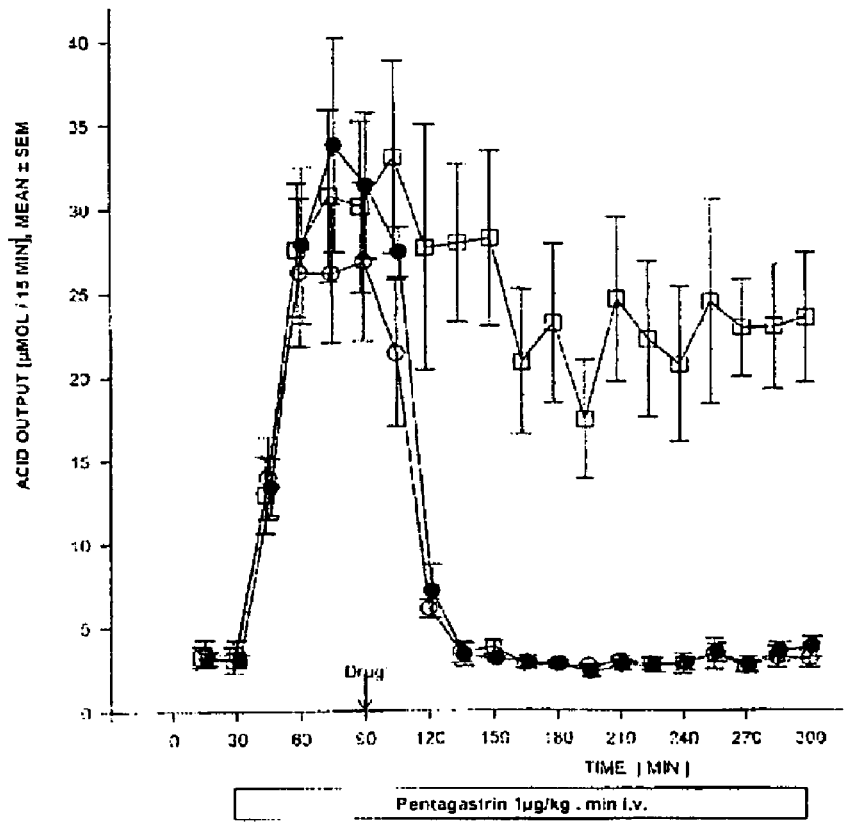
Figure 2: Acid inhibition by intravenous pantoprazole-Mg-enantiomeres. Drug administration 1 hour after commencement of pentagastrin stimulation.
(o) 1 µmol/kg iv (-) –pantoprazole-Mg;
(•) 1 µmol/kg iv (+) - pantoprazole-Mg;
(¬) Control

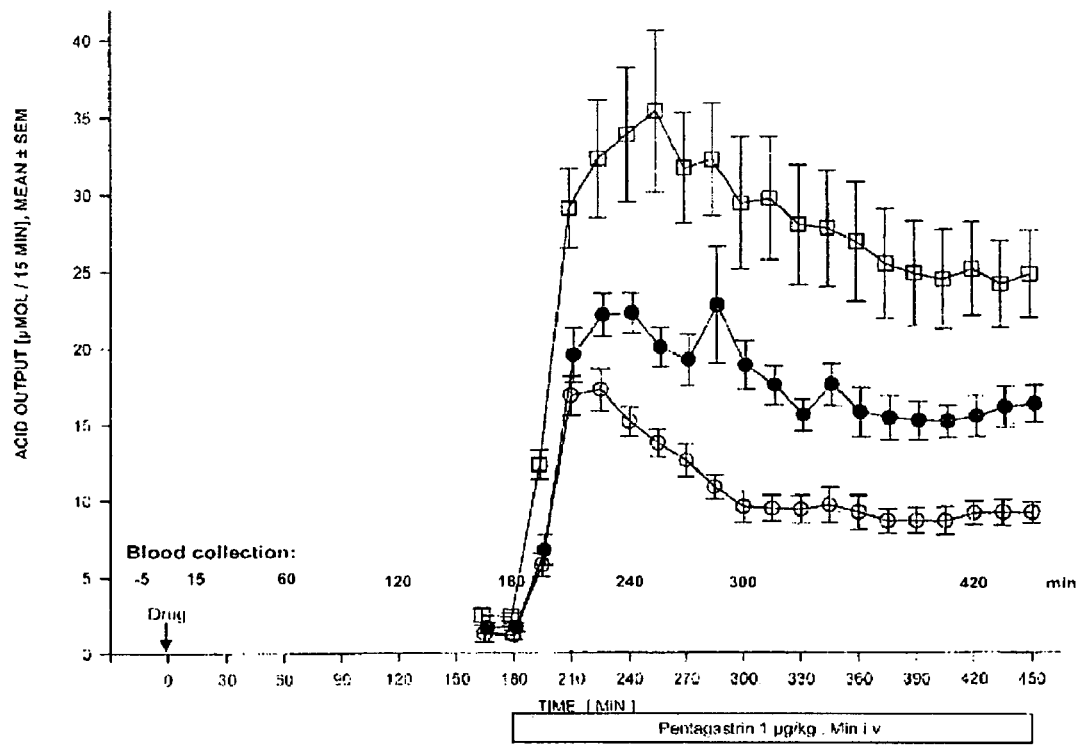
Figure 3: Influence of intravenous pantoprazole-Mg-enantiomeres.
Drug administration 3 hours before commencement of pentagastrin stimulation.
(○) 1 µmol/kg iv (-) –pantoprazole-Mg;
(●) 1 µmol/kg iv (+) - pantoprazole-Mg;
(□) Control

SALT OF (S)-PANTOPRAZOLE AND ITS HYDRATES

SUBJECT-MATTER OF THE INVENTION

The present invention relates to novel salts of the active compound (S)-pantoprazole. The novel salts can be used in the pharmaceutical industry for preparing medicaments.

BACKGROUND OF THE INVENTION

Owing to their $H^+/K^+$-ATPase-inhibitory action, pyridin-2-ylmethylsulphinyl-1H-benzimidazoles, such as those known, for example, from EP-A-0005129, EP-A-0166287, EP-A-0174726 and EP-A-0268956 are of considerable importance in the therapy of disorders associated with an increased secretion of gastric acid.

Examples of active compounds from this group which are commercially available or in clinical development are 5-methoxy-2-[(4-methoxy-3,5-dimethyl-2-pyridinyl)methylsulphinyl]-1H-benzimidazole (INN: omeprazole), (S)-5-methoxy-2-[(4-methoxy-3,5-dimethyl-2-pyridinyl)methylsulphinyl]-1H-benzimidazole (INN: esomeprazole), 5-difluoromethoxy-2-[(3,4-dimethoxy-2-pyridinyl)methylsulphinyl]-1H-benzimidazole (INN: pantoprazole), 2-[3-methyl-4-(2,2,2-trifluoroethoxy)-2-pyridinyl)methylsulphinyl]-1H-benzimidazole (INN: lansoprazole), 2-{[4-(3-methoxypropoxy)-3-methylpyridin-2-yl]methylsulphinyl}-1H-benzimidazole (INN: rabeprazole) and 5-methoxy-2-((4-methoxy-3,5-dimethyl-2-pyridylmethyl)sulphinyl)-1H-imidazo[4,5-b]pyridine (INN: tenatoprazole).

The above mentioned sulphinyl derivatives which, owing to their mechanism of action, are also referred to as proton pump inhibitors or, abbreviated, as PPI, are chiral compounds.

DESCRIPTION OF THE RELATED ART

For the first time, the international patent application WO92/08716 describes a chemical process, which allows pyridin-2-ylmethylsulphinyl-1H-benzimidazoles to be separated into their optical antipodes. The compounds mentioned as being prepared in an exemplary manner include, inter alia, the compounds (+)- and (−)-5-difluoromethoxy-2-[(3,4-dimethoxy-2-pyridinyl)methylsulphinyl]-1H-benzimidazole [=(+)- and (−)-pantoprazole]. The international patent application WO92/08716 mentions that the optical antipodes of the pyridin-2-ylmethylsulphinyl-1H-benzimidazoles, i.e. the (+)- and (−)-enantiomers or the (R)- and (S)-enantiomers, are useful as active compounds in medicaments for the treatment of gastrointestinal disorders. For the mode of application and the dosage of the active compounds, reference is made, inter alia, to the European patent 166 287.

The international patent applications WO94/24867 and WO94/25028 claim the use of the compounds (−)- and (+)-pantoprazole for treating gastric disorders in humans. Each stereoisomer is said to have medical advantages compared to the respective other stereoisomer. The descriptions also mention a number of different possible salts of the stereoisomers, and particular preference is given to the sodium salt.

In international patent application WO94/27988, certain salts of (+)- and (−)-omeprazole and methods for their preparation are disclosed.

The international patent application WO97/41114 describes a certain process for preparing magnesium salts of pyridin-2-ylmethylsulphinyl-1H-benzimidazoles. What is described in an exemplary manner is, inter alia, the preparation of the magnesium salt of racemic pantoprazole. According to the given analytical data, the salt that is prepared is racemic pantoprazole magnesium in anhydrous form.

The international patent application WO00/10995 describes the dihydrate of the magnesium salt of racemic pantoprazole.

A common property of all of the abovementioned PPI is their sensitivity to acids (ultimately essential for effectiveness) which becomes apparent in their strong tendency to decompose in a neutral and in particular an acidic environment, giving rise to intensely coloured decomposition products. In the past, there has been no lack of considerable efforts, in spite of the sensitivity of the PPI to acids, to obtain stable and storable oral dosage forms comprising these PPI. Such stable and storable oral dosage forms (for example tablets or capsules) are now obtainable. However, the preparation of these oral dosage forms is relatively complicated, and with respect to the packaging too, certain complicated precautions have to be taken so that the dosage forms are sufficiently stable on storage even under extreme storage conditions (for example in tropical regions at high temperatures and high atmospheric humidity). Furthermore, in the past, there has been no lack of efforts to tailor the release of the PPI in the human body in the best possible manner to the respective requirements.

BRIEF DESCRIPTION OF THE DRAWINGS

FIG. 1 is a chart which represents an X-ray powder diffraction diagram of (−)-pantoprazole magnesium dihydrate.

FIG. 2 is a chart which represents the acid inhibition achieved by intravenous administration of various pantoprazole magnesium enantiomers from zero to 300 minutes.

FIG. 3 is a chart which represents the acid inhibition achieved by intravenous administration of various pantoprazole magnesium enantiomers from approximately 150 to 450 minutes.

DESCRIPTION OF THE INVENTION

It has now been found that the sodium salt of (−)- or (S)-pantoprazole, which is particularly preferred in the international patent application WO 94/24867, does not form a stable storage form. During various attempts to obtain a stable oral dosage form for (−)-pantoprazole, it has now been found that the magnesium salt, in particular in hydrate form, has highly surprising stability properties, making it a particularly suitable candidate for use in solid or oral dosage forms. Compared to the sodium salt of (−)-pantoprazole, the magnesium salt has considerably improved stability properties. Thus, for example, (−)-pantoprazole magnesium dihydrate is, at 70° C., completely stable for one week and shows virtually no discolouration or decomposition, whereas over the same period of time and under identical conditions, the colour of the hydrate of (−)-pantoprazole sodium changes to brown, with formation of considerable amounts of decomposition products.

Furthermore, the (−)-pantoprazole magnesium hydrate, which is the preferred subject of the invention, is a non-hygroscopic salt having a defined water content of about 4.4%, which corresponds to that of the dihydrate, whereas (−)-pantoprazole sodium absorbs water depending on drying conditions and atmospheric humidity, and, correspondingly, its water content varies from 2 to 12%. This absorption of water is reversible, so that it is difficult to adjust an exact water content. Surprisingly, not only the (−)-pantoprazole sodium, but also the (−)-pantoprazole calcium shows these poor stability properties. The water content of (−)-pantoprazole calcium varies from 4-8% depending on drying conditions and atmospheric humidity.

Compared to the racemic pantoprazole magnesium dihydrate, the (−)-pantoprazole magnesium dihydrate has, surprisingly, better wettability. a considerably higher dissolution rate at pH 7-7.4 and, at pH 10, about tenfold better solubility.

Accordingly, the invention provides in a first aspect the magnesium salt of (−)-pantoprazole [=(S)-pantoprazole]. Preferably, the invention provides the magnesium salt (−)-pantoprazole [=(S)-pantoprazole] hydrates, i.e. the hydrates of the compound magnesium (−)-bis{[5-(difluoromethoxy)]-2-[(3,4-dimethoxy-2-pyridinyl)methylsulphinyl]-1H-benzimidazolide}. Here, particular emphasis is given to hydrates, which—after drying under reduced pressure at 50° C.—have a water content of from about 4.0 to about 6.7%, in particular from about 4.0 to about 5.5%. Particular preference is given to the hydrate form which has a water content of from about 4.0 to about 5.0%, in particular from about 4.2 to about 4.6%, which corresponds to a dihydrate.

(−)-Pantoprazole magnesium and its hydrates can be used for the treatment and prevention of all disorders, which can be treated or prevented by using PPI. In particular, (−)-pantoprazole magnesium and its hydrates can be used for treating gastric disorders. In this context, particular mention should be made of the relatively high stability of (−)-pantoprazole magnesium in the form of its dihydrate. On storage under atmospheric conditions, the sum of by-products in (−)-pantoprazole magnesium dihydrate remains virtually constant, whereas in the case of (−)-pantoprazole sodium, under identical conditions (storage at 60-70° C.) the purity (according to HPLC) decreases from 99.5 to 96-97%. This relatively high storage stability makes (−)-pantoprazole magnesium dihydrate particularly suitable for use in medicaments.

The hydrates of (−)-pantoprazole magnesium are prepared in a manner known per se by reacting (−)-pantoprazole with a magnesium base, for example a magnesium alkoxide, or from a readily soluble (−)-pantoprazole salt (for example (−)-pantoprazole sodium) using a magnesium salt in water or in mixtures of water with polar organic solvents (for example alcohols, preferably methanol, ethanol or isopropanol, or ketones, preferably acetone).

Magnesium salts suitable for use in the process are, for example, magnesium chloride, magnesium bromide, magnesium fluoride, magnesium iodide, magnesium formate, magnesium acetate, magnesium propionate, magnesium gluconate or magnesium carbonate. It is also possible to react magnesium alkoxides (for example magnesium methoxide, magnesium ethoxide, magnesium (iso)propoxide, magnesium butoxide, magnesium hexoxide or magnesium phenoxide) in an alkoholate medium with (−)-pantoprazole or (−)-pantoprazole sodium and to crystallise the (−)-pantoprazole magnesium hydrates by addition of water. Furthermore, it is possible to recrystallise the (−)-pantoprazole magnesium hydrates from, e.g., methanol/water mixtures.

For use in solid, in particular oral, pharmaceutical formulations, the (−)-pantoprazole magnesium hydrate according to the invention is milled in order to obtain crystals with a particle size distribution of 90%, preferably 99% below 100 μm.

According to the invention, "(−)-pantoprazole" is understood to include "(−)-pantoprazole, substantially free of the (+)-enantiomer".

The examples below illustrate the invention in more detail, without limiting it, m. p. denotes melting point, min. denotes minute(s), h denotes hour(s).

EXAMPLES

1. Magnesium (−)-bis{[5-(difluoromethoxy)]-2-[(3,4-dimethoxy-2-pyridinyl)methylsulphinyl]-1H-benzimidazolide} Dihydrate At 20-25° C., 20.2 g (52.7 mmol) of (−)-pantoprazole {(−)-[5-(difluoromethoxy)]-2-[(3,4-dimethoxy-2-pyridinyl)methylsulphinyl]-1H-benzimidazole} were suspended in 200 ml of purified water. A solution of (55.2 mmol) sodium hydroxide in 10 ml of water was added, and the mixture was stirred at 20-30° C. for 30 min. With addition of a filter aid (1 g Hyflo-Super-Cel), the turbid solution was filtered. 6.32 g (31.2 mmol) of magnesium dichloride hexahydrate in 150 ml of water were then added drop by drop with stirring over a period of 30 min. After a further 30 min., the precipitated solid was filtered off with suction using a suction filter, stirred with water (2×50 ml) and again filtered off with suction. Drying under reduced pressure at 50-60° C. gave, in a yield of 17.36 g (80%), a hydrate of magnesium (−)-bis{[5-(difluoromethoxy)]-2-[(3,4-dimethoxy-2-pyridinyl)methylsulphinyl]-1H-benzimidazolide} having a water content of 4.5-4.7% as a colourless to beige powder (m. p.158-161° C. with decomposition).

Specific rotation: $\alpha_D^{20°}=-114°$ (c=0.5, measured in methanol)

For recrystallisation, 1.88 g of the hydrate were, at 55° C. dissolved in 6 ml of methanol, and 20 ml of water were added with stirring. A colourless to beige solid crystallized out. This gave the title compound of m. p. 160-163° C. (with decomposition) having a water content of 4.3-4.4%.

Alternatively, the title compound can also be prepared from organic-aqueous solvent mixtures. To this end, (−)-pantoprazole sodium, or (−)-pantoprazole together with one equivalent of aqueous, for example 2N, sodium hydroxide solution, is dissolved in an organic solvent, for example warm acetone. 0.5 to 0.55 equivalents of a magnesium salt (for example magnesium chloride hexahydrate), dissolved in water, are added drop by drop, and the mixture is cooled with stirring. The precipitated solid is filtered off, washed with the solvent mixture in question and dried at 50° C. under reduced pressure until the weight remains constant. This gives the title compound as a colourless to beige powder.

2. Magnesium (−)-bis{[5-(difluoromethoxy)]-2-[(3,4-dimethoxy-2-pyridinyl)methylsulphinyl]-1H-benzimidazolide} Dihydrate A. (−)-Pantoprazole-Na 36 g of (−)-pantoprazole were suspended in 180 ml of methyl isobutyl ketone (MIBK) and 18 ml of 2-propanol and heated to an internal temperature of 45° C. The suspension was stirred at this temperature for 15 min. At 50° C., 11 g of 30% (w/w) aqueous sodium hydroxide solution were slowly added drop by drop to this suspension. A clear to slightly turbid solution resulted. This solution was stirred for a bit longer and then filtered to give a clear solution.

The clear filtrate was slowly cooled to room temperature. Between 45° C. and 30° C. crystallization, which could be accelerated by seeding with (−)-pantoprazole sodium, began. The resulting suspension was stirred at an internal temperature of <20° C. for another 2 h. The suspension was then filtered, and the crystals were washed with 40 ml of MIBK.

Drying was carried out in a vacuum drying cabinet at <50 mbar and 40-45° C. [It is also possible to dispense with drying and to use the moist product (having an MIBK content of 10-20%) directly for step B]. The white-beige crystalline product obtained after drying was hygroscopic. The water content was from 2 to 12%. The absorption and release of water were reversible. Yield: 34 g=90% of theory (based on anhydrous product). Specific rotation: $a_D{}^{20°}=-95$ (c=0.5, measured in methanol, sodium salt having a water content of 12%). m. p.: 145-165° C. (decomposition, sodium salt having a water content of 2%); 102-109° C. (decomposition, sodium salt having a water content of 12%).

B. (−)-Pantoprazole-Mg 30 g of (−)-pantoprazole sodium salt (calculated anhydrous substance) were suspended in 260 ml of water. The suspension was heated to 35-40° C. and stirred at 35-40° C. for another 10 min. This gave a clear solution. The clear solution was cooled to 22-27° C. 14.3 g of magnesium chloride hexahydrate were dissolved in 100 ml of water, and at room temperature and with stirring, the solution was slowly added dropwise to the (−)-pantoprazole sodium salt solution. The resulting suspension was then stirred at room temperature for another 4 h. The suspension was, under pressure, filtered through a Nutsche filter, and the product was, a little at a time, washed twice with 300 ml of water. Drying in a vacuum drying cabinet at <50 mbar and 40-45° C. gave 27.5 g (90%) of the title compound of m. p. 160-163° C. Water content 4.3-4.4%; specific rotation: $a_D{}^{20°}=-129$ (c=0.5, measured in methanol).

Recrystallisation of (−)-pantoprazole-Mg

For recrystallisation, 6.0 g of the (−)-pantoprazole-Mg-dihydrate were, at 55° C., dissolved in 18 ml of methanol. After 15 min, 90 ml of water were added with stirring to the orange-brown-solution. A colourless to beige solid crystallised out. The resulting suspension was then stirred at 20-25° C. for another 1 hour. The solid was filtered off, washed with 10 ml of water and dried under vacuum for 20 hours at 50° C. The yield for the title compound was 88% (5.26 g) with the following data:

M.P.: 161-165° C. (with decomposition)

Specific rotation: $a_D{}^{20°}=-130$ (c=0.5, measured in methanol)

XRD-Data: The X-ray powder diffraction patterns were measured on a Philips PW 1800 diffractometer at ambient temperature in the range of $3° \leq 2\phi \leq 80°$. The X-ray powder diffraction patterns of (−)-pantoprazole magnesium dihydrate, are characterized by reflections with strong ($2\phi$ about 23°), medium ($2\phi$ about 6°, 12°, 14°, 17°, 19°, 22°, 24°, 25°, 30°, 33° and 35°) and small ($2\phi$ about 13°, 16°, 26°, 28°, 33° and in the range of 36° to 62°) intensities. An exemplary X-ray powder diffraction diagram is shown in FIG. 1.

Commercial utility (−)-Pantoprazole magnesium and its hydrates have useful pharmacological properties, rendering them commercially utilizable. In particular, they have a pronounced inhibitory effect on the secretion of gastric acid and excellent gastrointestinal protective action in warm-blooded animals, in particular man. Here, the compounds according to the invention are distinguished by a highly selective action, an advantageous duration of action, a particularly high bioavailability, a metabolization profile that is uniform among different individuals, the lack of significant side-effects and a wide therapeutic spectrum.

In this context, "gastrointestinal protection" is to be understood as the prevention and treatment of gastrointestinal disorders, in particular gastrointestinal inflammatory disorders and lesions (such as, for example, Ulcus ventriculi, Ulcus duodeni, gastritis, irritable bowel owing to an increased production of acid or as a result of medicaments, GERD, Crohn's disease, IBD) which may be caused, for example, by microorganisms (for example Helicobacter pylori), bacterial toxins, medicaments (for example certain antiphlogistics and antirheumatic drugs), chemicals (for example ethanol), gastric acid or stress.

With their excellent properties. (−)-pantoprazole magnesium and hydrates thereof are, in various models for the determination of antiulcerogenic and antisecretory properties, surprisingly clearly superior to the prior art compounds, in particular with respect to their stability and their metabolization properties. Owing to these properties, (−)-pantoprazole magnesium and hydrates thereof are highly suitable fur use in human and veterinary medicine, where they are used, in particular, for the treatment and/or prophylaxis of gastrointestinal disorders.

Accordingly. the invention furthermore provides the use of (−)-pantoprazole magnesium and hydrates thereof for the treatment and/or prophylaxis of the abovementioned diseases.

The invention also embraces the use of (−)-pantoprazole magnesium and hydrates thereof for preparing medicaments used for the treatment and/or prophylaxis of the abovementioned diseases.

The invention also provides medicaments comprising (−)-pantoprazole magnesium and hydrates thereof.

The medicaments are prepared by processes known per se which are familiar to the person skilled in the art. As medicaments, (−)-pantoprazole magnesium hydrates are employed either as such or, preferably, in combination with suitable pharmaceutical auxiliaries or carriers in the form of tablets, coated tablets, capsules, suppositories, plasters (for example as TTS), emulsions, suspensions or solutions, where the content of active compound is advantageously from about 0.1 to about 95% and where it is possible to produce pharmaceutical dosage forms (for example flow-release forms or enteric forms) which, by the appropriate choice of auxiliaries and carriers, are tailored for the active compound and/or the desired onset of action and/or the duration of action.

The auxiliaries or carriers suitable for the desired pharmaceutical formulations are known to the person skilled in the art. In addition to solvents, gel formers, suppository bases, tabletting auxiliaries and other carriers for active compounds, it is possible to use, for example, antioxidants, dispersants, emulsifiers, antifoams, flavour-masking agents, preservatives, solubilizers, colorants or, in particular, permeation promoters and complex formers (for example cyclodextrins).

(−)-Pantoprazole magnesium and hydrates thereof can be administered orally, parenterally or percutaneously.

In human medicine, it has generally been found to be advantageous to administer (−)-pantoprazole magnesium hydrates, when given orally, in a daily dose of from about 0.1 to about 2, preferably about 0.2 to about 1.5 and in particular about 0.3 to about 1.1, mg/kg of body weight [based on (−)-pantoprazole], if appropriate in the form of a plurality of, preferably 1 to 4, individual doses, to obtain the desired result. For parenteral treatment, it is possible to use similar or (in particular when the active compounds are administered intravenously) generally lower dosages. The optimum dosage and the type of administration of the active compounds required in each case can easily be determined by the person skilled in the art.

A further aspect of the invention is thus a medicament, comprising a (−)-pantoprazole magnesium hydrate together with customary auxiliaries, where the single dose comprises from about 10 to about 100 mg of (−)-pantoprazole.

A further aspect of the invention is a medicament, comprising a (−)-pantoprazole magnesium hydrate together with customary auxiliaries, where the single dose comprises from about 20 to about 80 mg of (−)-pantoprazole.

A further aspect of the invention is the use of (−)-pantoprazole magnesium and hydrates thereof for treating gastrointestinal disorders.

A further aspect of the invention is the use of (−)-pantoprazole magnesium and hydrates thereof for treating gastrointestinal disorders in patients who are slow metabolizers.

A further aspect of the invention is the use of (−)-pantoprazole magnesium and hydrates thereof for treating gastrointestinal disorders in patients who have a risk of drug interactions.

A further aspect of the invention is the use of (−)-pantoprazole magnesium and hydrates thereof for treating gastrointestinal disorders in patients who need an inhibition of acid secretion for an extended period of time.

A further aspect of the invention is a medicament for treating gastrointestinal disorders for use in patients who are slow metabolizers, comprising a (−)-pantoprazole magnesium hydrate together with customary auxiliaries, where the single dose comprises from about 10 to about 100 mg of (−)-pantoprazole.

A further aspect of the invention is a medicament for treating gastrointestinal disorders for use in patients who are slow metabolizers, comprising a (−)-pantoprazole magnesium hydrate together with customary auxiliaries, where the single dose comprises from about 20 to about 80 mg of (−)-pantoprazole.

A further aspect of the invention is a medicament for treating gastrointestinal disorders for use in patients who have a risk of drug interactions, comprising a (−)-pantoprazole magnesium hydrate together with customary auxiliaries, where the single dose comprises from about 10 to about 100 mg of (−)-pantoprazole.

A further aspect of the invention is a medicament for treating gastrointestinal disorders for use in patients who have a risk of drug interactions, comprising a (−)-pantoprazole magnesium hydrate together with customary auxiliaries, where the single dose comprises from about 20 to about 80 mg of (−)-pantoprazole.

A further aspect of the invention is a medicament for treating gastrointestinal disorders for use in patients who need an inhibition of acid secretion for an extended period of time, comprising a (−)-pantoprazole magnesium hydrate together with customary auxiliaries, where the single dose comprises from about 10 to about 100 mg of (−)-pantoprazole.

A further aspect of the invention is a medicament for treating gastrointestinal disorders for use in patients who need an inhibition of acid secretion for an extended period of time, comprising a (−)-pantoprazole magnesium hydrate together with customary auxiliaries, where the single dose comprises from about 20 to about 80 mg of (−)-pantoprazole.

If (−)-pantoprazole magnesium and hydrates thereof are to be used for treating the abovementioned diseases, the pharmaceutical preparations may also comprise one or more pharmacologically active ingredients from other groups of medicaments. Examples that may be mentioned include tranquilizers (for example from the group of the benzodiazepines, e. g., diazepam), spasmolytic drugs (e. g., bietamiverine or camylofine), anticholinergic drugs (e. g., oxyphencyclimine or phencarbamide), local anesthetics (e. g., tetracaine or procaine), and optionally also enzymes, vitamins or amino acids.

In this context, particular emphasis is given to the combination of the compounds according to the invention with other pharmaceuticals which buffer or neutralize gastric acid or which inhibit the secretion of acid, such as, for example, antacids (such as, for example, magaldrate) or $H_2$ blockers (e. g., cimetidine, ranitidine), and with gastrin antagonists with the aim to enhance the main action in an additive or superadditive-sense and/or to eliminate or reduce side-effects or to obtain a more rapid onset of action. Mention may also be made of the fixed or free combination with NSAIDs (such as, for example, etofenamate, diclofenac, indometacin, ibuprofen or piroxicam) for preventing the gastrointestinal damage caused by the NSAIDs, or with compounds, which modify gastrointestinal motility, or with compounds, which reduce the incidence of transient lower esophageal sphincter relaxation (TLOSR), or with antibacterial substances (such as, for example, cephalosporins, tetracyclins, penicillins, macrolides, nitroimidazoles or else bismuth salt) for controlling Helicobacter pylori. Antibacterial combination partners that may be mentioned include, for example, mezlocillin, ampicillin, amoxicillin. cefalothin, cefoxitin, cefotaxim, imipenem, gentamycin, amicacin, erythromycin, ciprofloxacin, metronidazole, clarithromycin, azithromycin and combinations thereof (e. g., clarithromycin+metronidazole or amoxicillin+clarithromycin).

Pharmacological Investigations

1. Metabolization on Human Liver Microsomes

I. Materials and methods

I) Human liver microsomes: Pantoprazole racemate and the (+)- and (−)-enantiomers (10 μM each) were incubated with human liver microsomes (source: TEBU, incubation in 1 mg/ml protein, 100 mM Tris-HCl, pH 7.4, 1 mM $NADPH_2$). Reaction was terminated after 30 and 120 minutes by liquid nitrogen, the parent compound was detected by HPLC (10 mM $KH_2PO_4$, pH 7.4, acetonitril gradient 20-48%).

II) Recombinant CYP 2C19 (source: GENTEST); incubation method as described under I) (in presence of 0.1 mg/ml protein).

III) Recombinant CYP 3A4 (source: GENTEST); incubation method as described under I) (in presence of 0.3 mg/ml protein).

II. Results (−)-Pantoprazole (26%, mean, n=3, SD=3, 120 min) was significantly less metabolized on human microsomes compared to the (+) enantiomer (44%, mean n=3, SD=2, 120 min) and the racemate (44%. mean, SD=4, 120 min), respectively. Similarly, on CYP2C19 the values were for: (−)-pantoprazole (54%, mean, n=3, SD=3, 120 min); (+)-pantorazole: (64, mean, n=3, SD=5, 120 min); racemate (67%, mean, n=3, SD=1, 120 min). The biotransformation on CYP3A4 was not different among the enantiomers and the racemate.

The lower biotransformation rate of (−)-pantoprazole compared to the (+) enantiomer lets expect a lower biotransformation in vivo as well with the result of higher plasma levels of (−)-pantoprazole. Clinically, this may translate into an even lower risk for drug interactions for (−)-pantoprazole.

2. Inhibition of Acid Output in the Ghosh-Schild Rat After I.V. Administration

I. Introduction

Pyridin-2-ylmethylsulphinyl-1H-benzimidazoles are chiral compounds. The two enantiomers, which exist for each pyridin-2-ylmethylsulphinyl-1H-benzimidazole, are pro-drugs that require acid-catalyzed activation into a sulfenamide, which is achiral and for both enantiomers identical. The achiral sulfenamide then reacts covalently with cysteines of the gastric proton pump to block it. Hence, in pharmacodynamic terms, the two enantiomers should display identical potencies and efficacies, provided they are in vivo metabolized at the same rate. This was assumed in case of pantoprazole based on rat data that have shown almost identical percentage inhibitions by the two enantiomers of the sodium salt (see Kromer, W., Scand. J. Gastroenterol. 2001, 36, suppl. 234: 3-9, FIG. 5). Such previous experiments covered 3.5 hours following intravenous drug administration and have now been repeated with the two enantiomers of the magnesium salt of pantoprazole. In addition, the effects of the two enantiomers of the magnesium salt of pantoprazole have now been determined in the time interval between 3 and 7.5 hours following i.v. administration of 1 µmol/kg of the magnesium salts of the two enantiomers.

II. Materials and methods.

Female Sprague Dawley CD rats (190-210 g body weight) were anaesthetised with 1.5 g/kg i.m. of urethane, in 5 ml/kg physiologic saline. The trachea was intubated and both, the left external jugular vein (for drug administration) and left femoral vein (for pentagastrin infusion) were cannulated. An esophagus/cardia-cannula (diameter: 1.7 mm) was inserted transorally, and a pylorus-cannula (diameter: 2.6 mm) was inserted through the duodenum, and both were secured with a ligature. The pyloric catheter was led through the right abdominal wall. Body temperature was maintained at 37.0±0.2° C. by means of infrared radiation and electric cushion (automatic infinite control via rectal temperature probe). After thorough flushing (about 50-100 ml), the stomach was continuously perfused with 0.5 ml/min of physiologic saline (37° C.). In the effluate, collected at 15 min intervals, the pH as well as the acid output were determined, the latter by titration to pH 7 with freshly prepared 0.01 N NaOH.

Gastric secretion was stimulated by a continuous intravenous infusion (left femoral vein) of 1 µg/kg×min pentagastrin (in 1.6 ml/h physiologic saline) starting after determination of two basal values of acid secretion, i.e., 30 min after commencement of stomach perfusion. See horizontal bars in FIGS. 1 and 2 for pentagastrin-infusion. 1 µmol/kg of (−)-pantoprazole or (+)-pantoprazole-Mg was administered intravenously in a volume of 1 ml/kg body weight as an 30 sec i.v. injection. Controls received the corresponding amount of physiologic saline. Note that 1 µmol pantoprazole-Mg is equivalent to 2 µmol of the free acid of pantoprazole.

Experiment 1: Drug administration 1 hour after commencement of pentagastrin stimulation (see FIG. 2).

Experiment 2: Drug administration 3 hours prior to commencement of pentagastrin stimulation (see FIG. 3).

III. Results

FIG. 2 of Experiment 1 clearly shows that the two enantiomers of pantoprazole-Mg are equieffective in blocking acid output during the first 3.5 hours following drug administration 1 hour after commencement of pentagastrin stimulation.

In Experiment 2, where the drug was administered 3 hours prior to commencement of acid stimulation by pentagastrin, and acid output was measured over the following 4.5 hours, it was found, surprisingly, that the (−)-enantiomer was significantly superior to the (+)-enantiomer in inhibiting acid secretion (FIG. 3).

The (−)-enantiomer is significantly more effective than the (+)-enantiomer in the time interval between 3 and 7.5 hours after drug administration. It is important to note that this difference in favour of the (−)-enantiomer is maintained and still significant even 7.5 hours after i.v. drug administration.

This unexpected finding could be explained for example, if the preferential and favourable binding of pantoprazole to cysteine 822 of the proton pump was mainly due to the binding of its (−)enantiomer. This could be therapeutically exploited by administering the (−)-enantiomer of pantoprazole in order to achieve a longer duration of action, compared to the racemate or to the other PPIs that do not bind to cysteine 822 at all (Shin, J. M., and Sachs. G., Gastroenterology 2002, 123: 1588-1597).

The invention claimed is:

1. (−)-Pantoprazole magnesium [(S)-pantoprazole magnesium] dihydrate, wherein (−)-pantoprazole magnesium is substantially free of the (+)-enantiomer.

2. A (−)-pantoprazole magnesium dihydrate according to claim 1, having a water content of from about 4.0 to about 5.0%.

3. A (−)-pantoprazole magnesium dihydrate according to claim 1, having a water content of from about 4.2 to about 4.6%.

4. A (−)-pantoprazole magnesium dihydrate according to claim 1 with a particle size distribution of 99% below 100 µm.

5. A (−)-pantoprazole magnesium dihydrate according to claim 1 with X-ray powder diffraction patterns which are characterized by reflections with strong (2φ about 23°), medium (2φ about 6°, 12°, 14°, 17°, 19°, 22°, 24°, 25°, 30°, 33° and 35°) and small (2φ about 13°, 16°, 26°, 28°, 33° and in the range of 36° and 62°) intensities.

6. A pharmaceutical composition comprising (−)-pantoprazole magnesium dihydrate, wherein (−)-pantoprazole magnesium is substantially free of the (+)-enantiomer, together with a suitable pharmaceutical auxiliary or carrier.

7. A pharmaceutical composition comprising (−)-pantoprazole magnesium dihydrate, wherein (−)-pantoprazole magnesium is substantially free of the (+)-enantiomer, together with a suitable pharmaceutical auxiliary or carrier, wherein (−)-pantoprazole is present in an amount from about 10 to about 100 mg.

8. A method of treating a gastrointestinal disorder in a patient comprising administering to a patient in need thereof a therapeutically effective amount of (−)-pantoprazole magnesium dihydrate, wherein (−)-pantoprazole magnesium is substantially free of the (+)-enantiomer and wherein the patient needs an inhibition of acid secretion for an extended period of time.

9. A (−)-pantoprazole magnesium dihydrate according to claim 2 with a particle size distribution of 99% below 100 µm.

10. A (−)-pantoprazole magnesium dihydrate according to claim 3 with a particle size distribution of 99% below 100 µm.

11. A (−)-pantoprazole magnesium dihydrate according to claim 2 with X-ray powder diffraction patterns which are characterized by reflections with strong (2φ about 23°), medium (2φ about 6°, 12°, 14°, 17°, 19°, 22°, 24°, 25°, 30°, 33° and 35°) and small (2φ about 13°, 16°, 26°, 28°, 33° and in the range of 36° and 62°) intensities.

12. A (−)-pantoprazole magnesium dihydrate according to claim 3 with X-ray powder diffraction patterns which are characterized by reflections with strong (2φ about 23°), medium (2φ about 6°, 12°, 14°, 17°, 19°, 22°, 24°, 25°, 30°, 33° and 35°) and small (20φ about 13°, 16°, 26°, 28°, 33° and in the range of 36° and 62°) intensities.

13. A pharmaceutical composition comprising a (−)-pantoprazole magnesium dihydrate according to claim 2 together with a suitable pharmaceutical auxiliary or carrier.

14. A pharmaceutical composition comprising a (−)-pantoprazole magnesium dihydrate according to claim 2 together with a suitable pharmaceutical auxiliary or carrier, wherein (−)-pantoprazole is present in an amount from about 10 to about 100 mg.

15. A pharmaceutical composition comprising a (−)-pantoprazole magnesium dihydrate according to claim 3 together with a suitable pharmaceutical auxiliary or carrier.

16. A pharmaceutical composition comprising a (−)-pantoprazole magnesium dihydrate according to claim 3 together with a suitable pharmaceutical auxiliary or carrier, wherein (−)-pantoprazole is present in an amount from about 10 to about 100 mg.

17. A pharmaceutical composition comprising a (−)-pantoprazole magnesium dihydrate according to claim 4 together with a suitable pharmaceutical auxiliary or carrier.

18. A pharmaceutical composition comprising a (−)-pantoprazole magnesium dihydrate according to claim 4 together with a suitable pharmaceutical auxiliary or carrier, wherein (−)-pantoprazole is present in an amount from about 10 to about 100 mg.

19. A pharmaceutical composition comprising a (−)-pantoprazole magnesium dihydrate according to claim 5 together with a suitable pharmaceutical auxiliary or carrier.

20. A pharmaceutical composition comprising a (−)-pantoprazole magnesium dihydrate according to claim 5 together with a suitable pharmaceutical auxiliary or carrier, wherein (−)-pantoprazole is present in an amount from about 10 to about 100 mg.

\* \* \* \* \*